(12) United States Patent
Eldered et al.

(10) Patent No.: US 7,676,019 B2
(45) Date of Patent: Mar. 9, 2010

(54) COMPRESSION ARRANGEMENT

(75) Inventors: Kjell Eldered, Ingarö (SE); Torbjörn Hjärn, Vaxholm (SE)

(73) Assignee: Sectra Mamea AB, Kista (SE)

( * ) Notice: Subject to any disclaimer, the term of this patent is extended or adjusted under 35 U.S.C. 154(b) by 225 days.

(21) Appl. No.: 11/669,933

(22) Filed: Jan. 31, 2007

(65) Prior Publication Data

US 2008/0181361 A1 Jul. 31, 2008

(51) Int. Cl.
*A61B 6/04* (2006.01)
(52) U.S. Cl. ........................................... 378/37
(58) Field of Classification Search ............ 378/20, 378/37, 79, 208
See application file for complete search history.

(56) References Cited

U.S. PATENT DOCUMENTS

| 5,386,447 | A | * | 1/1995 | Siczek | 378/37 |
| 5,526,394 | A | * | 6/1996 | Siczek et al. | 378/37 |
| 6,611,575 | B1 | * | 8/2003 | Alyassin et al. | 378/37 |
| 6,876,879 | B2 | * | 4/2005 | Dines et al. | 600/427 |
| 6,999,553 | B2 | * | 2/2006 | Livingston | 378/37 |
| 2006/0245541 | A1 | * | 11/2006 | Aubel | 378/37 |

* cited by examiner

*Primary Examiner*—Irakli Kiknadze
(74) *Attorney, Agent, or Firm*—Fox Rothschild LLP

(57) ABSTRACT

The present invention relates to a compression arrangement for use in an x-ray imaging apparatus, the arrangement comprising a compression paddle and an actuator for displacing said compression paddle in a distance, said paddle having an extension direction substantially transverse to an object insertion direction. The actuator is operatively arranged to incline said paddle along said extension direction.

32 Claims, 14 Drawing Sheets

COMPRESSION ARRANGEMENT

TECHNICAL FIELD

The present invention relates to a compression paddle in a compression apparatus for use in a breast imaging apparatus for pressing the breast of the patient to be examined.

BACKGROUND OF THE INVENTION

In mediolateral oblique view (MLO) the image is taken from an oblique or angled view. During routine screening mammography, the MLO view is preferred over a lateral 90-degree projection because more of the breast tissue can be imaged in the upper outer quadrant of the breast and the axilla (armpit).

The present invention introduces a new compression apparatus and compression paddle to obtain better leveling of the breast tissue in MLOs, and fully taking advantage of the image field in tomosynthesis, which is three-dimensional x-ray imaging.

In x-ray imaging, in particular tomosynthesis, the image field is not shaped as a box. A typical shape is rather a section of a cone with a rectangular cross-section. One problem for the compression paddle edge path with respect to the x-ray field is that the compression paddle is normally wider than the ray field. The width of the field from the x-ray source increases with respect to its height with increasing base section, because the x-ray source scans from one side to the other side.

If the object (breast) is thick, the paddle must be higher up in the x-ray field, where the field is wider. Consequently, the paddle must be wider than the widest field boundary to avoid intersecting of the image. If the object is thin, the paddle will extend outside the object board when it is lowered close to the board.

This is not a problem in CC-positioning, i.e. the patient is standing and the table is horizontal. The problem occurs when positioning with angled examination table, MLO, which may have an angle of 45-60 degrees, to be able to imagine pectoral muscles.

US 2006/0262899 discloses a compression paddle comprising a paddle base, a paddle wall comprising a first side-wall, and a second side-wall. The first side-wall and/or the second side-wall are disposed upon the paddle base and inclined with respect to the paddle base at an angle that is effective to permit an x-ray beam uninterrupted access to an object of interest located on an opposing side of the paddle base from an x-ray source when an angle between a central axis of the x-ray beam and a vertical taken at an inner surface of the first side-wall and/or the inner surface of the second side-wall is about 15 degrees to about 75 degrees. Although the breast compression paddles are for use in mammography systems, including standard and tomosynthesis mammography systems, the invention does not solve all the problems, especially related to MLO, in particular for tomosynthesis.

SUMMARY OF THE INVENTION

In case of MLO, the compression paddle must extend as little as possible so that it does not press against the shoulder of the patient but against the breast. With a breast having maximum thickness (e.g. 100 mm), the compression paddle will not travel all the way down more than a distance such that both side edges of the paddle are within the x-ray field.

Thus, the present invention according to the preferred embodiments solves the general problem of positioning the compression paddle within the x-ray field and more especially when the examination area is tilted sidewise, for example in MLO examination. An aspect of the present invention is automatic setting for the compression arrangement, depending on what kind of image to acquire, such as CC or left or right MLO. The settings may be automatically selected depending on tilt of the system, or information from a computer for controlling said apparatus.

The problem is solved by means of a compression arrangement for use in an x-ray imaging apparatus, the arrangement comprising a compression paddle and an actuator for displacing said compression paddle in a distance. The actuator is operatively arranged to incline said paddle when displacing the paddle in said distance with respect to a vertical axis said paddle. The arrangement is for use in a mediolateral oblique view (MLO) apparatus. The arrangement of the invention is use in a mammography imaging apparatus.

According to one embodiment, the arrangement may further comprise a first and a second actuator arm connected to said paddle at end portions of said paddle and said arms being arranged to move independently in said displacement direction.

According to one embodiment, the arrangement may further comprise a first and a second actuator arm connected to said paddle, said arms being arranged to rotate around each rotating axis, and said paddle being slidebly connected to said first and second arms. The first and second arms may be arranged to rotate in different direction. The paddle may be suspended on said first and second arms. The paddle may be supported by said first and second arms. The first and second arms can be arranged in parallel. The first and second arms can rotate in same direction.

The arrangement may further comprise a first and a second actuator arm connected to said paddle, said arms being arranged to be displaced on a guide, and said paddle being slidebly connected to said first and second arms. The guide is arch-shaped.

The arrangement may further comprise a pressure sensor. A controlling arrangement may be provided for equalizing the pressure of said paddle with respect to the object thickness.

The invention also relates to an x-ray apparatus comprising an x-ray source, a compression arrangement and an object support. The compression arrangement comprises a compression paddle and an actuator arrangement, wherein said compression paddle is arranged to be displaced towards said object support in such a way that at least one edge of said paddle is displaced in inside and substantially along a boundary of an angled x-ray field from said x-ray source. The object support may be arranged to rotate. The object support may have a curved surface. The compression paddle may have a curved surface. The x-ray source is arranged to rotate with respect to said object support. Most preferably, the x-ray apparatus is a MLO apparatus.

BRIEF DESCRIPTION OF THE DRAWINGS

The present invention will be described with reference to attached drawings illustrating a number of non-limiting embodiments, in which.

DETAILED DESCRIPTION OF PREFERRED EMBODIMENTS

Figure 1A:
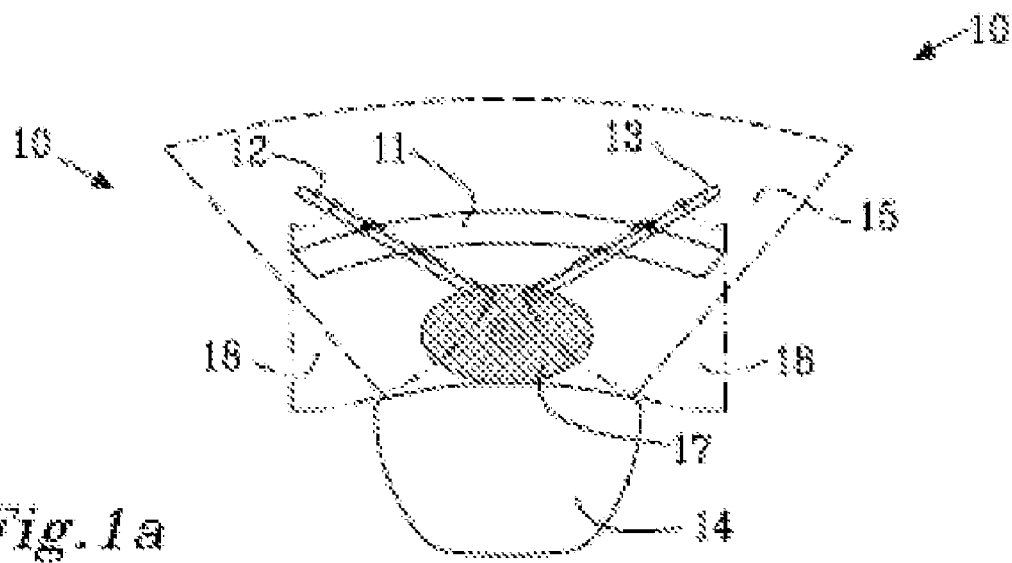
FIGS. 1a-1d schematically illustrate a first embodiment of the invention.
Figure 1B:
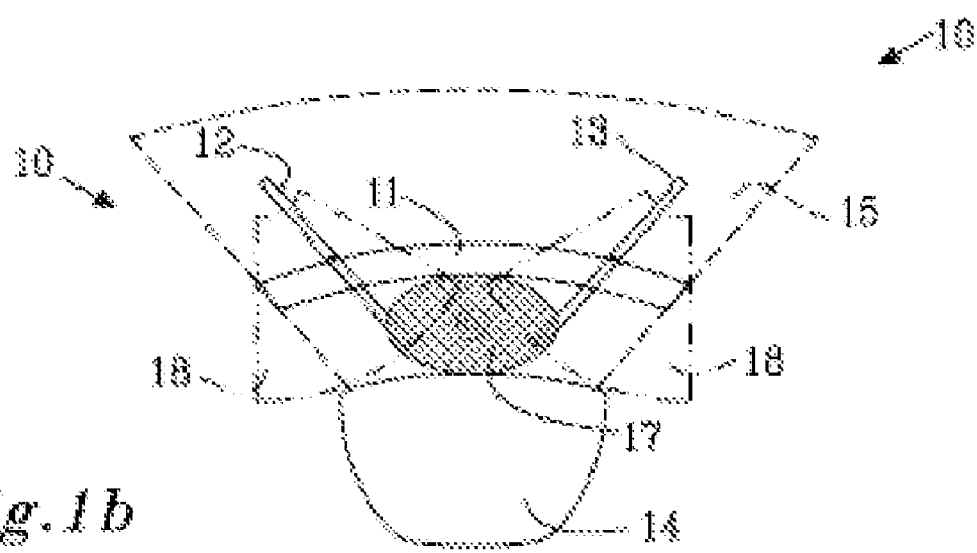

In the following description of exemplary embodiments like reference numerals refer to same functional parts.

For thinner breasts the paddle is lowered so that one edge at one side is within the field as it is illustrated in the drawings showing different embodiments.

Figure 5:
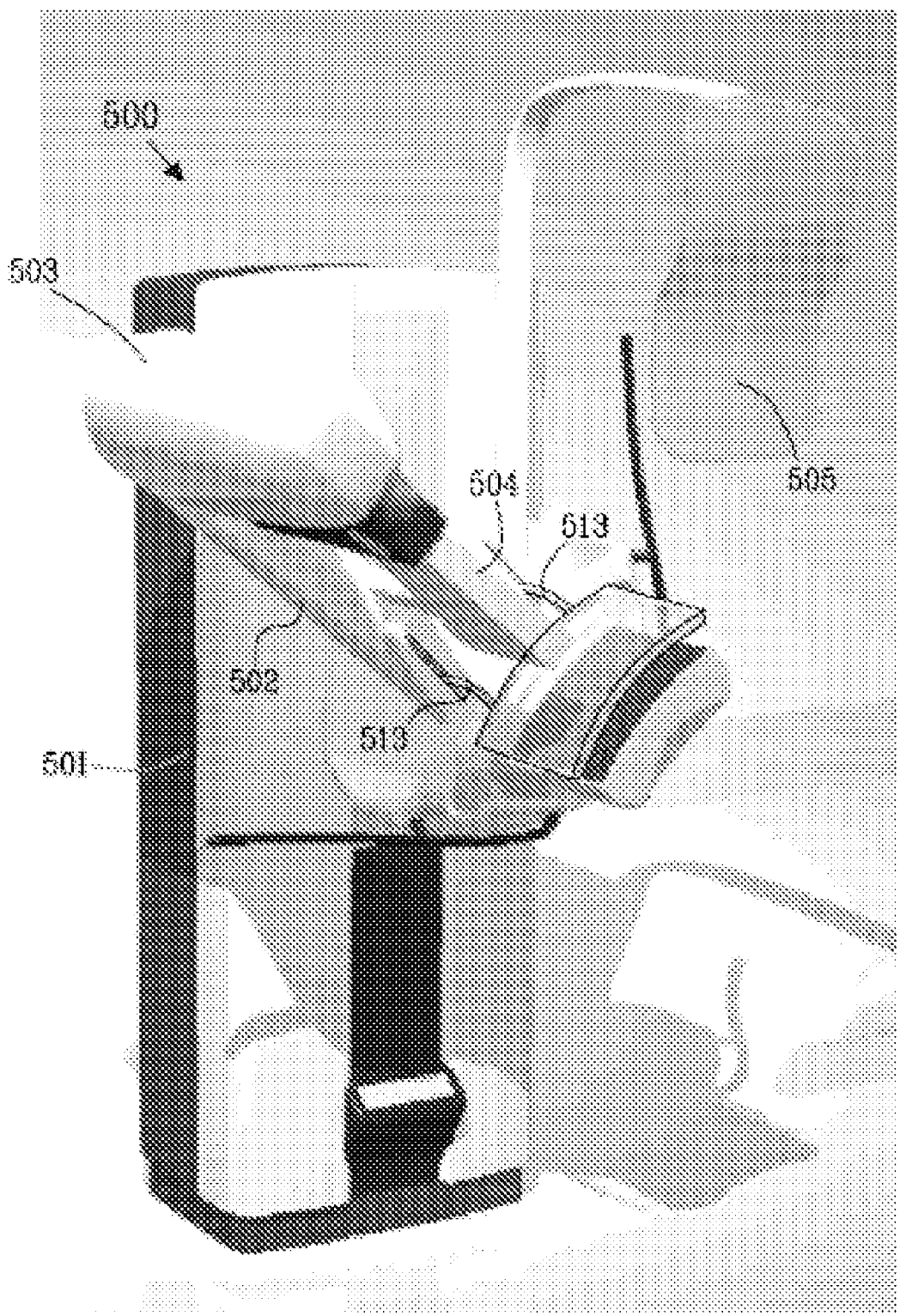
FIG. 5 is an x-ray apparatus employing a compression arrangement according to the invention, FIGS. 6a-6i schematically illustrate operation stages of an x-ray apparatus according to the invention, and FIG. 7 schematically illustrates a fifth embodiment of the invention.

FIG. 5 illustrates an exemplary embodiment of an x-ray apparatus 500 for mammography examination and especially for MLO examination. The x-ray apparatus comprises a stand 501, a rotateable examination part 502 comprising an x-ray source 503 radiation shield 504, an object bed 514, compression paddle 511, actuator arms 513 and protection shield 505. A rotating motor (not shown) is arranged inside the stand 501 and motor(s) (not shown) for actuating arms 513 are provided inside the housing of the examination part 502. Furthermore, inside the object bed detector arrays (not shown) are arranged for receiving x-rays and generating signal corresponding to object information. Moreover, the x-ray shield comprises a collimator (not shown) at its end.

The displacement of the compression paddle can be done in several ways. The important issue is that the compression paddle edge path with respect to the x-ray field is within of the ray field, which increases with respect to its height.

FIGS. 1a-1d illustrate stages in a first embodiment of the compression apparatus 10 having a compression paddle 11 and actuator arms 12 and 13. The compression apparatus is for use in an MLO mammography imaging apparatus for example, which comprises a tiltable so called object bed 14 on which the breast 17 rests. The object bed is slightly curved at the upper side receiving the breast. The compression paddle is also curved, substantially having same shape as the object bed. The compression paddle extends in a direction transverse to the direction in which the breast is inserted into the examination area. The dashed area 15 illustrates the x-ray radiation field from an x-ray source (not shown). The dashed-dotted areas 18, illustrate the operation area of the actuator arms 12 and 13.

Figure 1C:
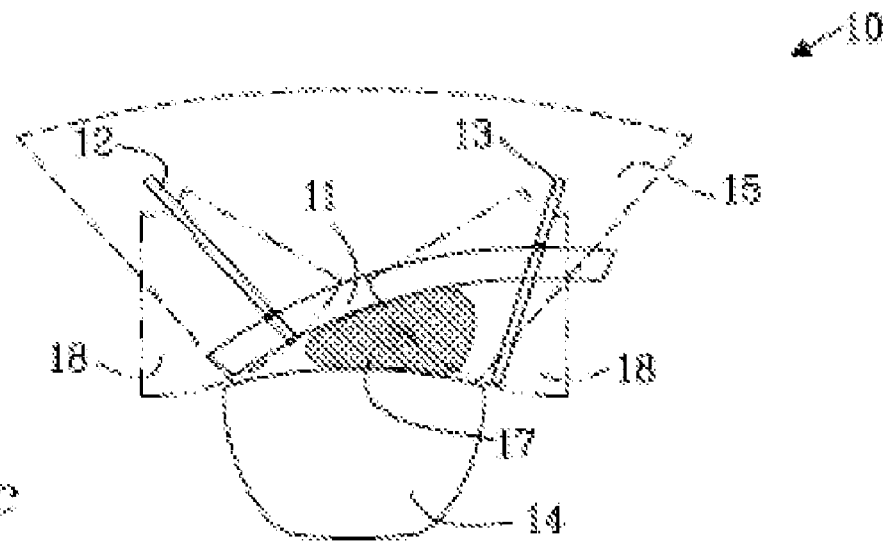
Figure 1D:
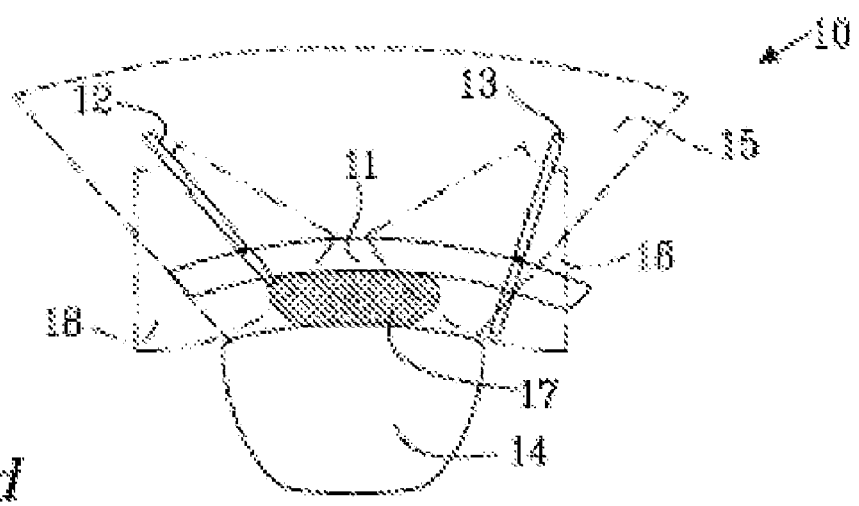

Pressure is applied while rotating the actuator arms 12 and 13 (clockwise and anti-clockwise, respectively) around a pivot on one end of the arms. The compression paddle is slidably connected to the arms and due to the rotation of the arms moves downwards towards the object bed 14. To allow the compression paddle edge (in this case left side edge) to follow the x-ray radiation field, the left arm stops at a suitable position while right arm continues rotating (anti-clockwise) and displaces (left side moving downwards and the right side upwards) the compression paddle towards the object board. The breast 17 is compressed from left side (FIG. 1c).

Figure 2A:
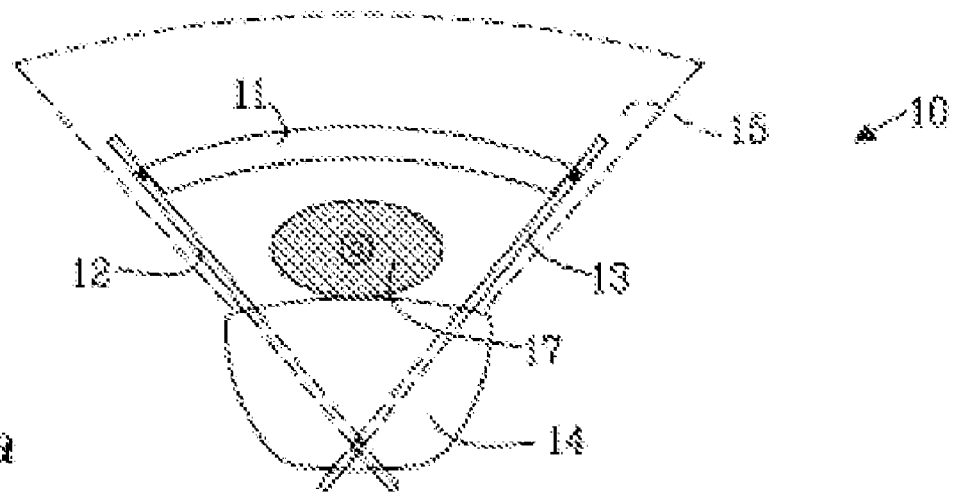
FIGS. 2a-2c schematically illustrate a second embodiment of the invention.
Figure 2B:
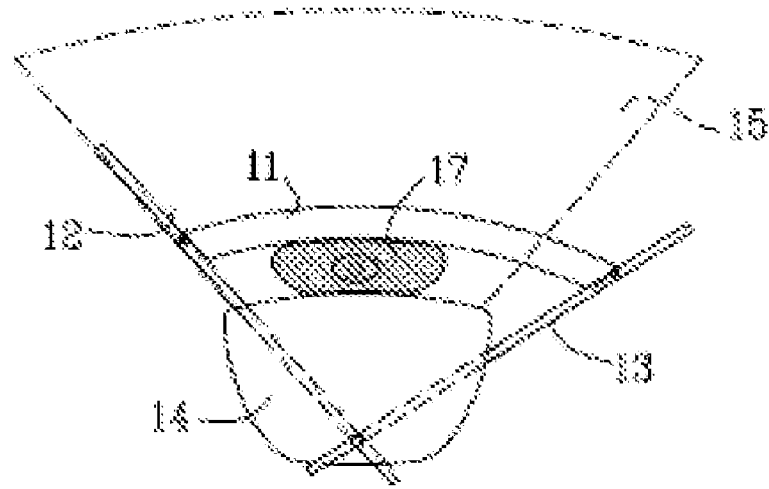
Figure 2C:
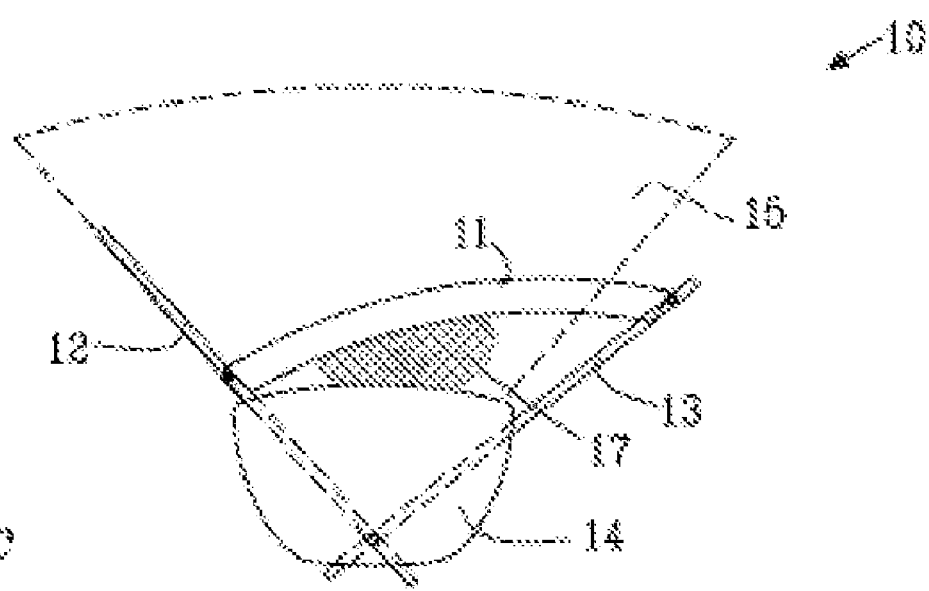

FIGS. 2a-2c illustrate a second embodiment in which the pressure paddle 11 is displaced by means of two actuator arms 12 and 13. If the left side of the paddle is to be lowered, the actuator arm 13 is arranged to rotate around a pivot at its one end portion, while actuator arm 12 is stationary, substantially extending along the angle of the x-ray field 15. The paddle 11 slidably attached to arm 12 is the lowered along the arm 12 while arm 13 rotates and drags the paddle along the arm 12 and thus compresses the breast 17. If the right side of the paddle is to be lowered, the arms 12 and 13 swap operation position. If the paddle is lowered vertically, both arms 12 and 13 rotate in opposite direction with same rotation angle. In FIG. 2c, the compression paddle is inside the x-ray field, with at least one of its edges (e.g. its image disturbing parts) immediately outside the x-ray field when compressing the breast during x-ray imaging. The other edge is within the x-ray field but not the breast image field and excluded from the image.

Figure 3A:
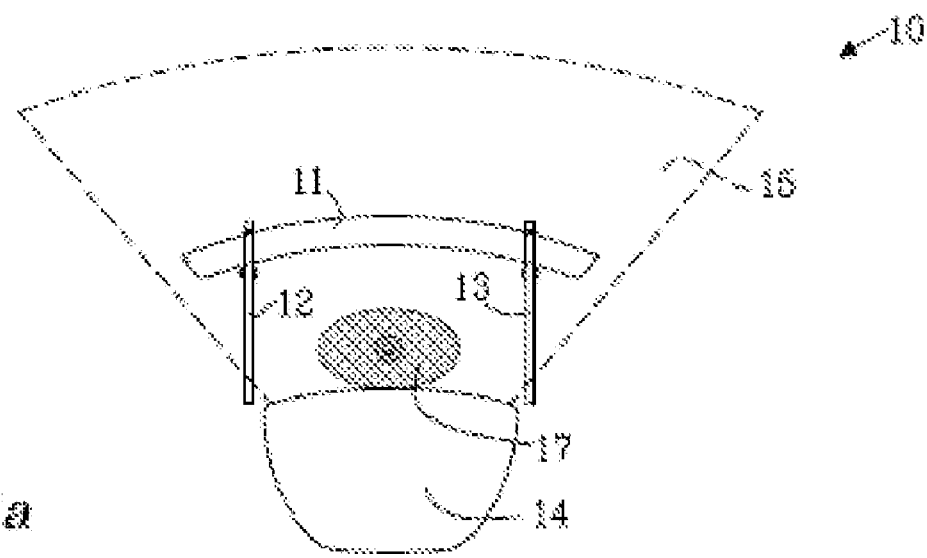
FIGS. 3a-3d schematically illustrate a third embodiment of the invention.
Figure 3B:
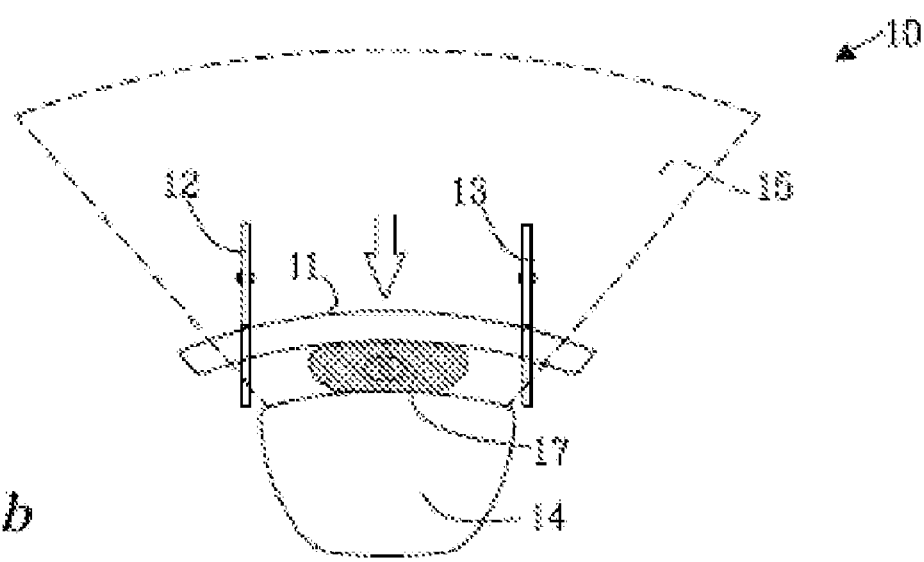
Figure 3C:
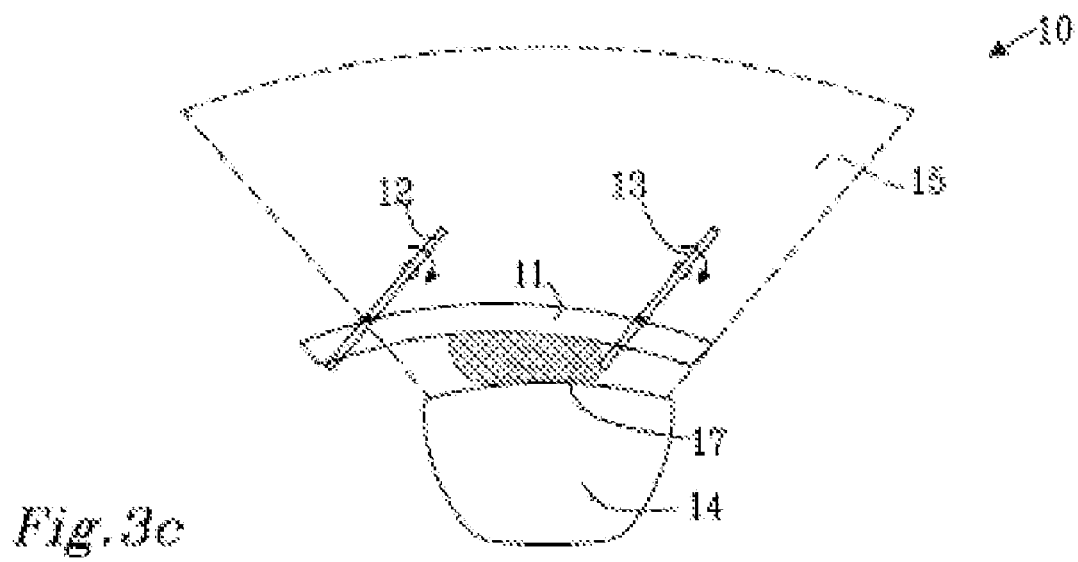
Figure 3D:
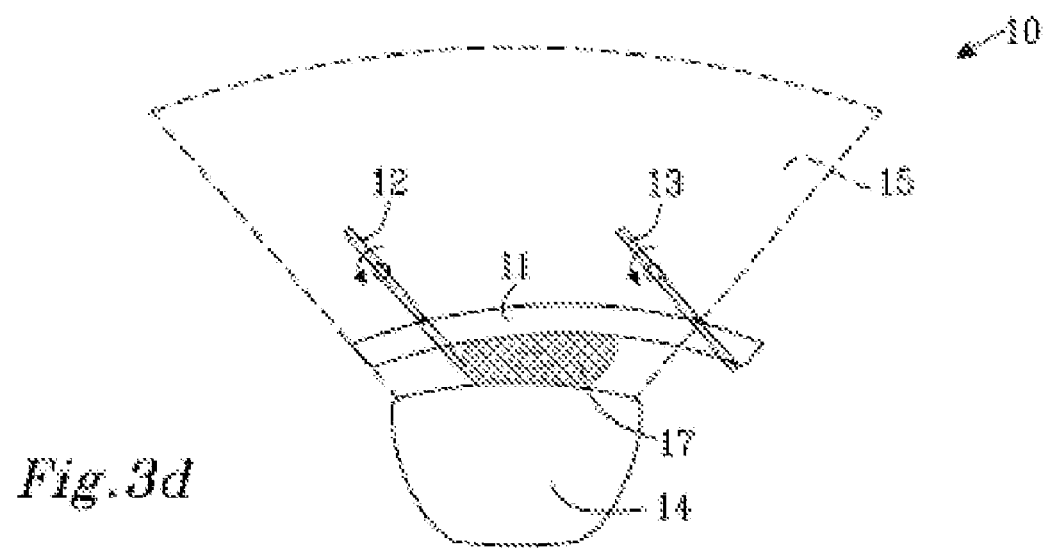

In the embodiment of FIGS. 3a-3c, the arms 12 and 13 are arranged substantially parallel and operate as guides and the arms are arranged in same angle as one edge of the field 15 spreading. The paddle 11 is displaced using, for example an actuator such as a third arm or a motor (not illustrated). The paddle is displaced along the arms and with one edge within the field boundary. In FIG. 3b the arms are substantially perpendicular to the object bed 14 and the paddle is displaced vertically. The compression paddle is inside the x-ray field, with both of its edges (e.g. its image disturbing parts) immediately outside the x-ray field when compressing the breast during x-ray imaging. In FIG. 3c the arms are rotated to left and the paddle is displaced with its right edge within the field edge. In FIG. 3d the arms are rotated to right and the paddle is displaced with its left edge within the field edge. The compression paddle is inside the x-ray field, with at least one of its edges (e.g. its image disturbing parts) immediately outside the x-ray field when compressing the breast during x-ray imaging. The other edge is within the x-ray field but not the breast image field and excluded from the image.

Figure 4A:
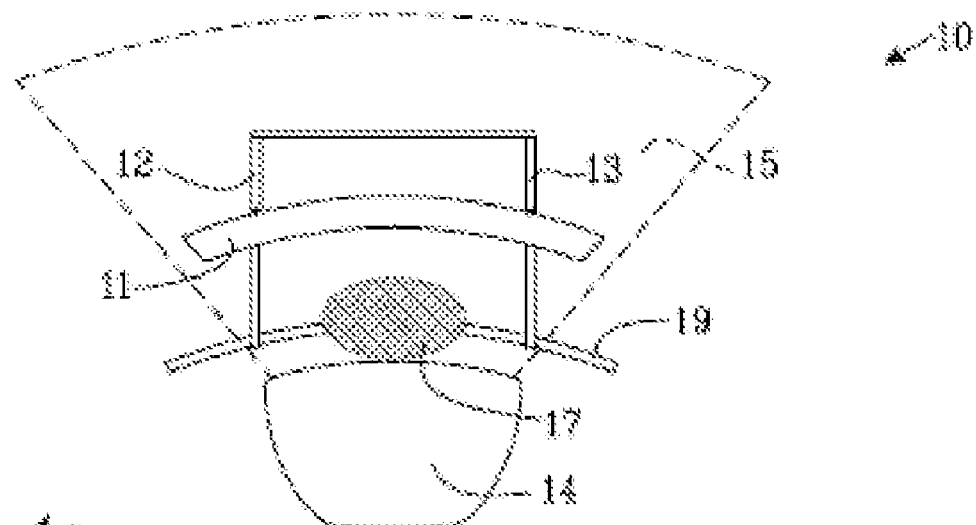
FIGS. 4a-4c schematically illustrate a fourth embodiment of the invention.
Figure 4B:
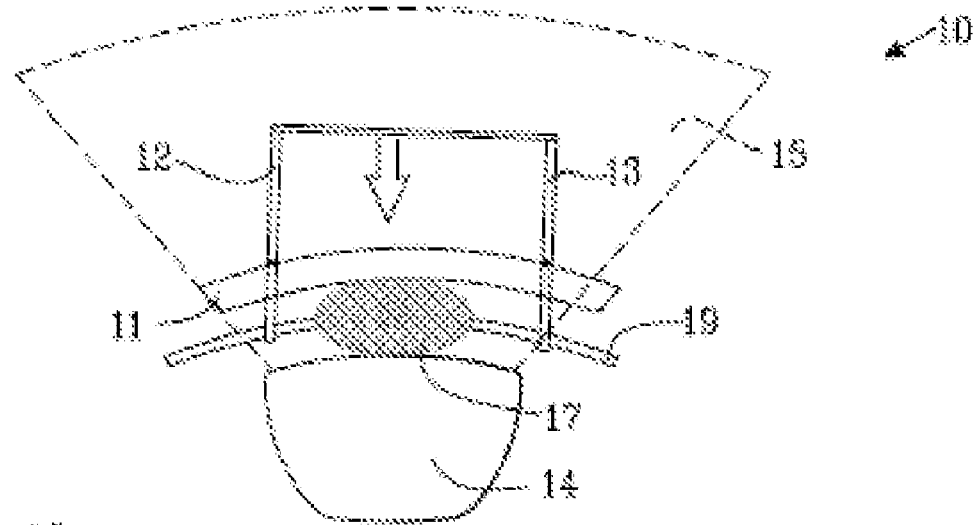
Figure 4C:
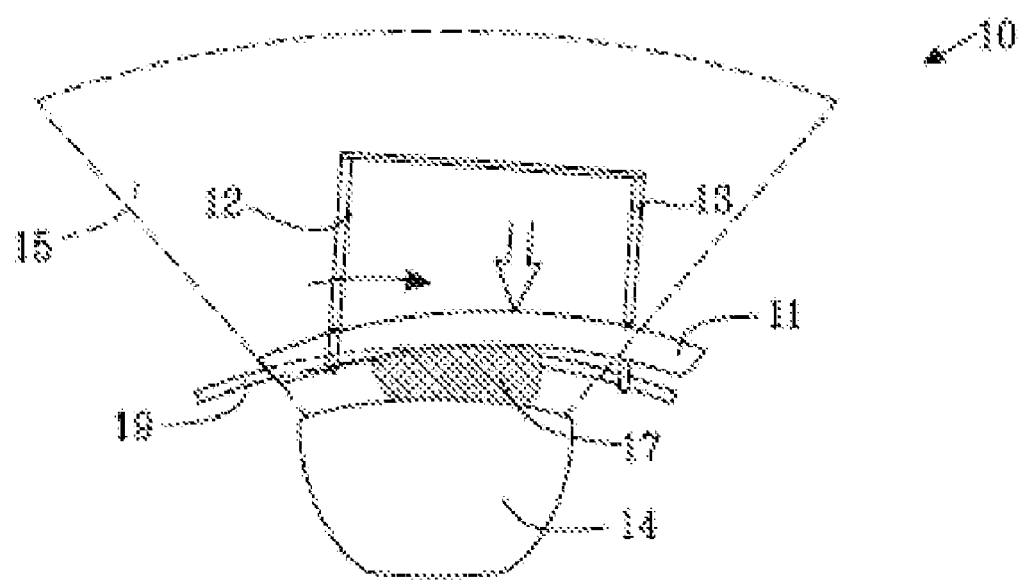

In the embodiment of FIGS. 4a-4c, the arms 12 and 13 are arranged parallel on an arched guide 19. The paddle 11 is arranged to move vertically along the arms 12 and 13. The paddle is further angled and lowered by moving the arms 12 and 13 along the arched guide 19.

In FIG. 4b, the paddle 11 is displaced vertically while the arms 12 and 13 are positioned substantially perpendicular to the object bed 14 and compress the breast 17 uniform over the object bed. The compression paddle is inside the x-ray field, but both of its edges (e.g. its image disturbing parts) immediately outside the x-ray field when compressing the breast during x-ray imaging. In FIG. 4c, the arms are displaced (to right) on the arched guide 19 while the paddle is moved vertically towards the object bed 14 and consequently the breast 17 is compressed at right side while the left edge of the paddle 11 is within the field 15. In FIG. 4d, the arms are displaced (to left) on the arched guide 19 while the paddle is moved vertically towards the object bed 14 and consequently the breast 17 is compressed at left side while the left right of the paddle 11 is within the field 15. In FIG. 4c, the compression paddle is inside the x-ray field, with at least one of its edges (e.g. its image disturbing parts) immediately outside the x-ray field when compressing the breast during x-ray imaging. The other edge is within the x-ray field but not the breast image field and excluded from the image.

In the simplest and general embodiment the compression paddle is moved using actuators which allow displacing the paddle in an angle with respect to its horizontal axis, such that one edge of the paddle has longer distance to the object bed than the other edge, i.e. one edge follows the x-ray field and is within the x-ray field.

Figure 7:
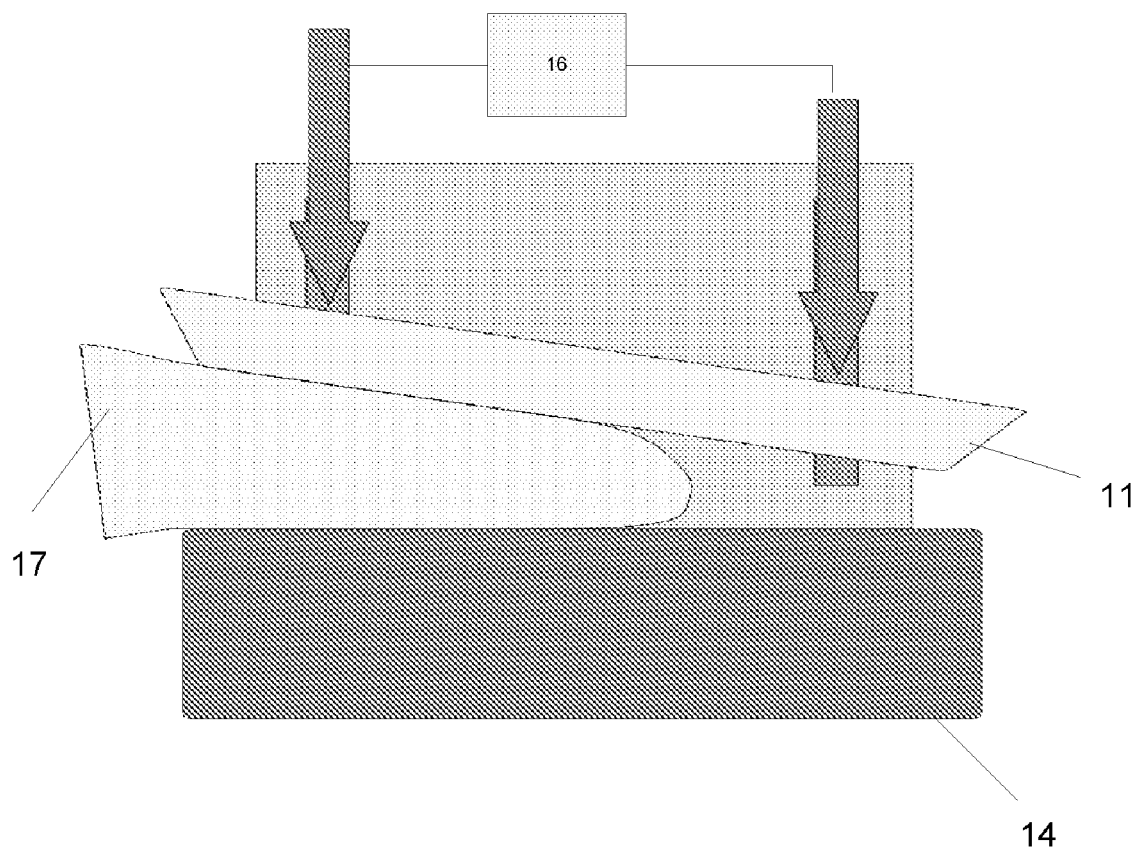

FIG. 7 illustrates an embodiment of a compression mechanism allowing conventional compressing by pressing both edges of the paddle 11 in same distance to the object bed 14 or by applying different forces to each arm and thus displacing the paddle 11 in different distances to the object bed 14. In this case, a force sensor 16 can be used to measure the force applied by each arm. The force sensor reads the force applied by each arm. A controller can use the output of the force sensor and control the arms to apply a uniform pressure with respect to the tissue thickness, i.e. the thin portion of the breast is compressed with respect to the breast thickness.

FIGS. 6a to 6i illustrate the operation of a MLO comprising a compression arrangement according to the present invention. The breast to be examined is not shown.

Figure 6A:
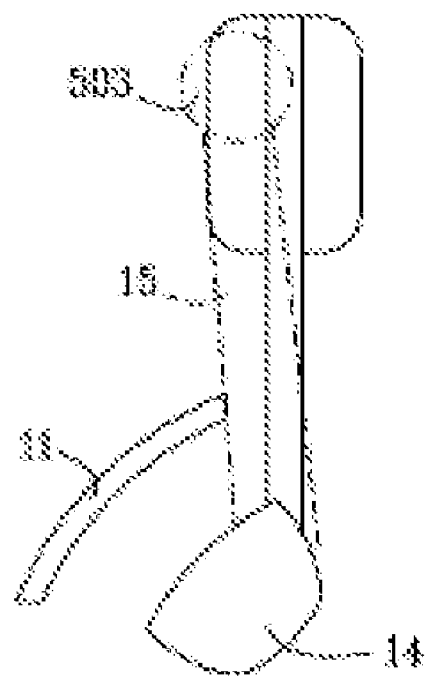

In FIG. 6a the object bed 14 is tilted to left and the compression paddle 11 is elevated to allow reception of the breast.

Figure 6B:
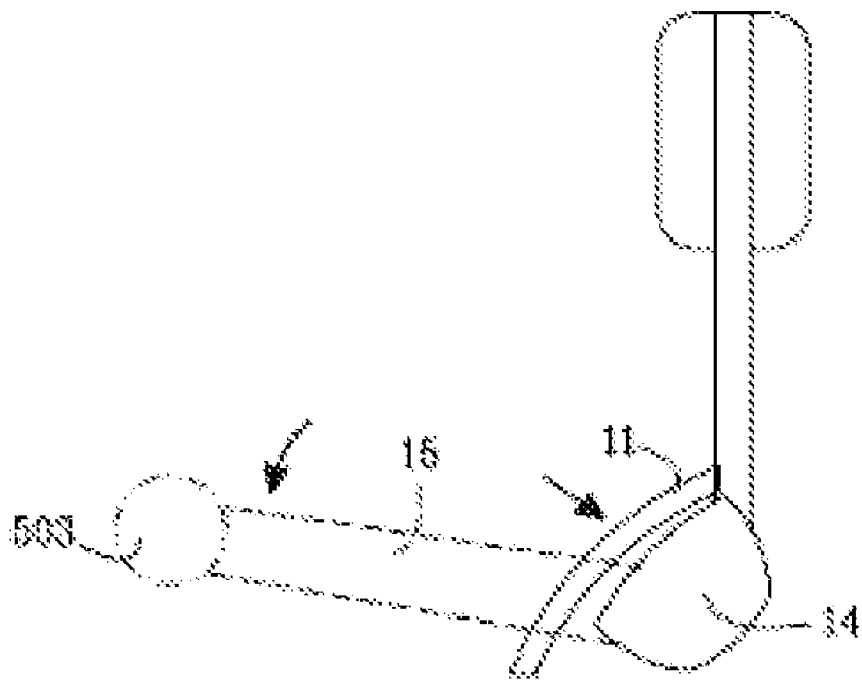

In FIG. 6b, the compression paddle 11 is lowered as described in the previous examples. When the breast is fixed, the x-ray source 503 radiates the examination area from right to left in a rotation movement. The dashed area 15 is the radiation field.

Figure 6C:
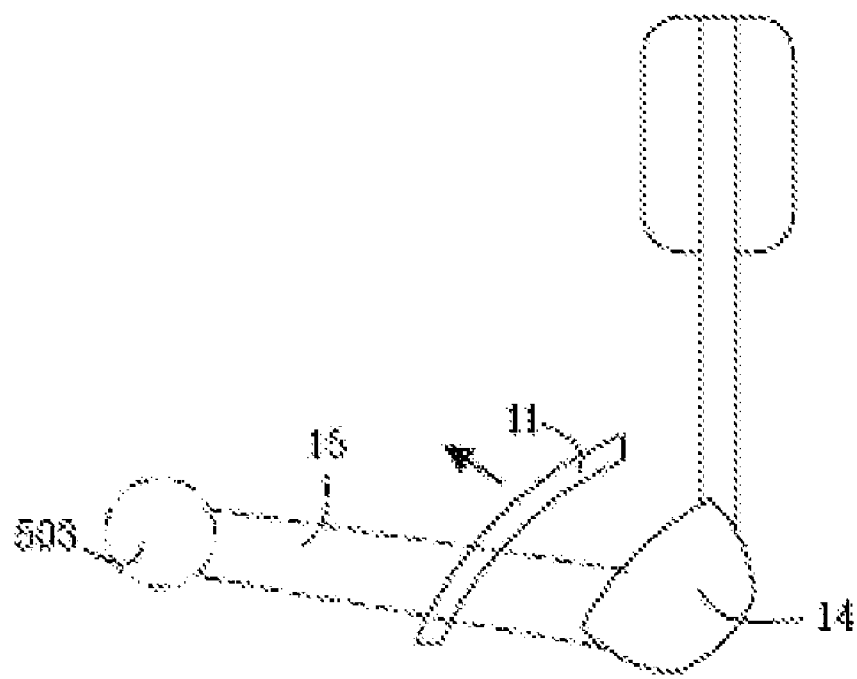

In FIG. 6c, the imaging sequence is terminated and the compression paddle is elevated.

Figure 6D:
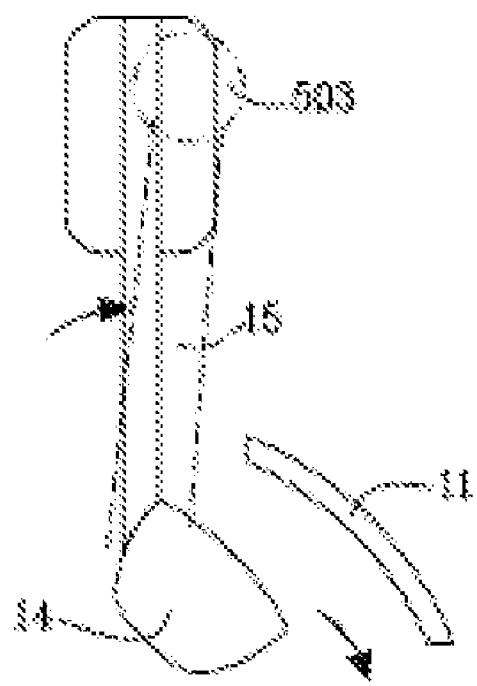

In FIG. 6d, the object bed 14 is rotated to an opposite position, i.e. from left to right.

Figure 6E:
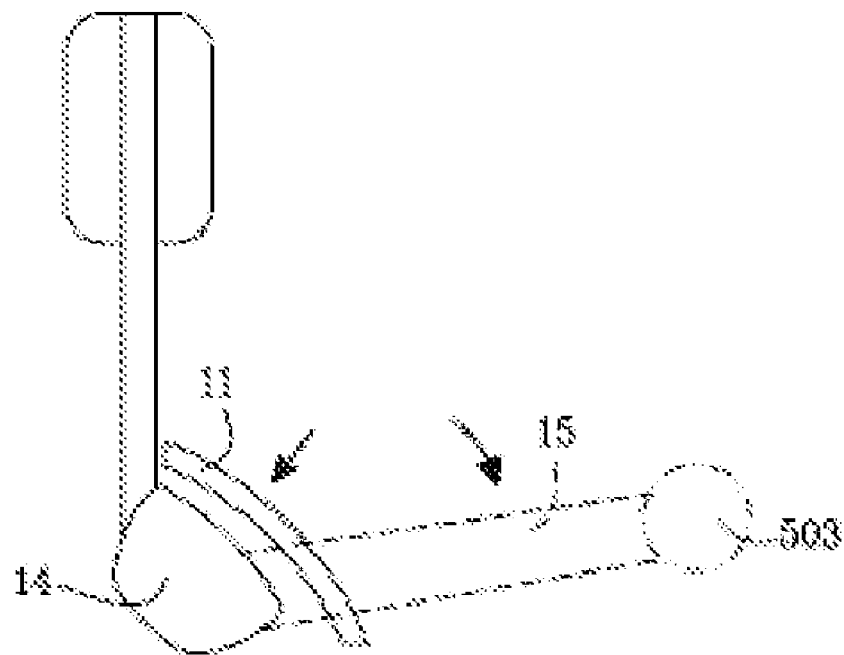

In FIG. 6e, the compression paddle 11 is lowered as described in the previous examples. When the breast is fixed, the x-ray source 503 radiates the examination area from left to right in a rotation movement.

Figure 6F:
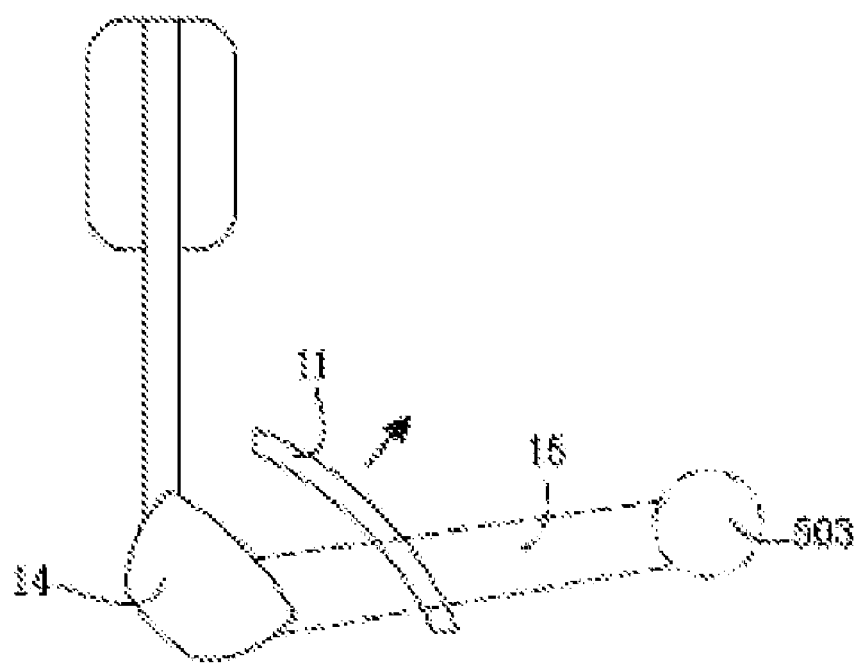

In FIG. 6f, the imaging sequence is terminated and the compression paddle is elevated.

Figure 6G:
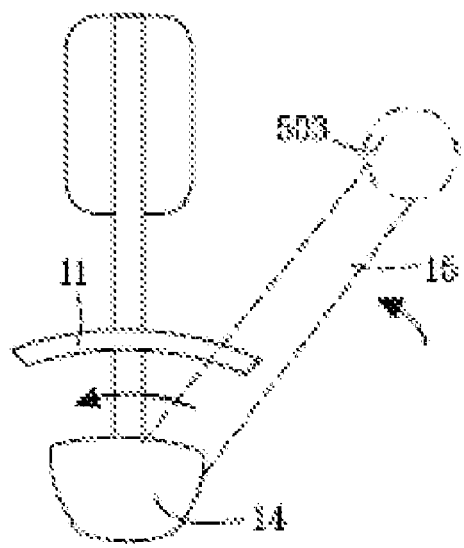

In FIG. 6g, the object bed 14 is rotated to a central position, i.e. it is horizontally positioned.

Figure 6H:
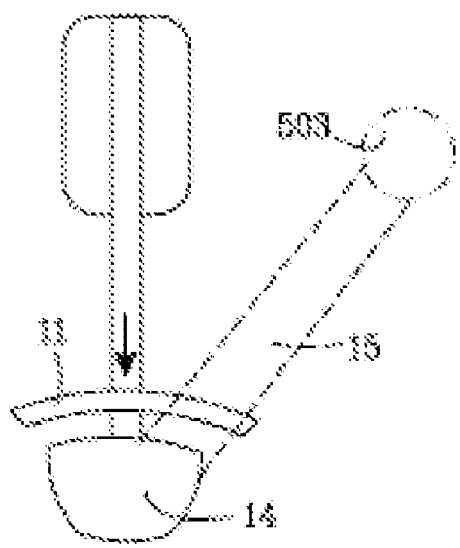

In FIG. 6h, the compression paddle 11 is lowered and allowing compressing the breast uniformly. When the breast is fixed, the x-ray source 503 radiates the examination area from left to right in a rotation movement.

Figure 6I:
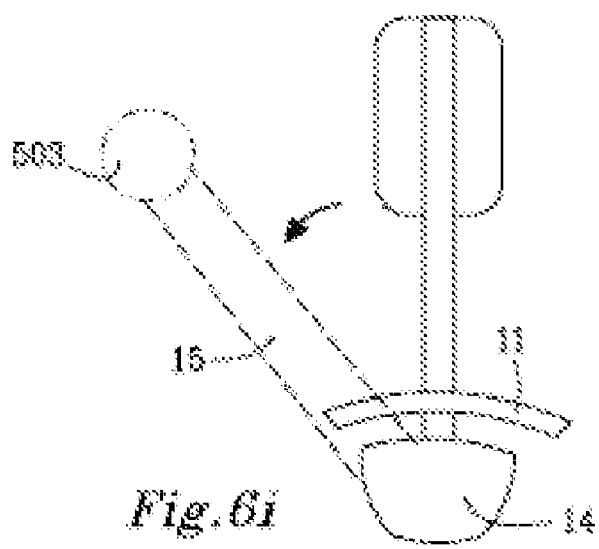

In FIG. 6i, the imaging sequence is terminated and the compression paddle is elevated.

The compression paddle may have only one actuator arm extending laterally and arranged in a central point or an end section which rotates the paddle for applying pressure as mentioned earlier.

All the preferred embodiments of the present invention comprise a means for automatically adjusting the mode of operation for said compression arrangement, depending on image type such as laterality. In one embodiment of the present invention, a control computer requests a certain mode for operation simultaneously as it requests a rotation of said x-ray apparatus to a position suitable for the requested type of examination. In another embodiment of the present invention, the compression arrangement sets its mode of operation depending on tilt of the x-ray apparatus, which in turn depends on the type of examination.

The invention may also realized in an x-ray apparatus for three-dimensional imaging of a human breast. The compression arrangement comprises a compression paddle, a guide and an actuator arrangement for displacement of the compression paddle along the guide. The direction of the guide can be adjustable, whereby an edge of the compression paddle essentially follows the angled boundary of a three-dimensional image field. An arrangement for automatically setting the direction of the guide depending on an angle of the apparatus or type of the examination may be provided.

It is obvious for a skilled person, that the invention is not limited to the described and illustrated embodiments and may be varied within the scope of the attached claims. It is thus possible to combine one or several of the embodiments.

What we claim is:

1. A compression arrangement for use in an x-ray imaging apparatus, said arrangement comprising a compression paddle and an actuator for displacing said compression paddle, said paddle extending in an object insertion direction and in a direction substantially transverse to said object insertion direction, wherein said actuator is operatively arranged to tilt said paddle in said direction transverse to said object insertion direction.

2. The arrangement of claim 1, for use in a Mediolateral Oblique View (MLO) or other tilted angle of said apparatus.

3. The arrangement of claim 1, for use in a breast imaging apparatus.

4. The arrangement of claim 1, comprising a first and a second actuator arm connected to said paddle at end portions of said paddle and said arms being arranged to move independently in the paddle displacement direction.

5. The arrangement of claim 1, comprising a first and a second actuator arm connected to said paddle, said arms being arranged to rotate around each rotating axis, and said paddle being slidebly connected to said first and second arms.

6. The arrangement of claim 5, wherein said first and second arms are arranged to rotate in different direction.

7. The arrangement of claim 5, wherein said paddle is suspended on said first and second arms.

8. The arrangement of claim 5, wherein said paddle is supported by said first and second arms.

9. The arrangement of claim 5, wherein said first and second arms are arranged in parallel.

10. The arrangement of claim 5, wherein said first and second arms rotate in same direction.

11. The arrangement of claim 1, comprising a first and a second actuator arm connected to said paddle, said arms being arranged to be displaced on a guide, and said paddle being slidebly connected to said first and second arms.

12. The arrangement of claim 11, wherein said guide is arc-shaped.

13. The arrangement of claim 1, further comprising a sensor for measurement of compression force or pressure.

14. The arrangement of claim 1, further comprising a controlling arrangement for equalizing the pressure of said paddle with respect to the object thickness.

15. The x-ray apparatus of claim 1, wherein said actuator arrangement is operatively arranged to incline said paddle with respect to said object support when displacing said paddle towards said object support.

16. The arrangement of claim 1, said compression paddle is inside the x-ray field, with at least one of its edges immediately outside the x-ray field when compressing the object during x-ray imaging.

17. An x-ray apparatus comprising an x-ray source, a compression arrangement and an object support, an image field volume with a first and a second angled boundary, wherein said compression arrangement comprises a compression paddle, an actuator arrangement for moving said paddle along a first or a second trajectory, a trajectory selector for automatically selecting said trajectory before said paddle reaches said image field volume, wherein all of said trajectories are essentially towards said support, and furthermore said first trajectory is essentially parallel to said first angled boundary, and said trajectory is essentially parallel to said second angled boundary.

18. The x-ray apparatus of claim 17, wherein said object support is arranged to rotate.

19. The x-ray apparatus of claim 17, wherein said object support has a curved surface.

20. The x-ray apparatus of claim 17, wherein said compression paddle has a curved surface.

21. The x-ray apparatus of claim 17, wherein said x-ray source is arranged to rotate with respect to said object support.

22. The x-ray apparatus of claim 17, wherein said actuator arrangement comprises a first and a second actuator arm connected to said paddle, said arms being arranged to be displaced on a guide, and said paddle being slidebly connected to said first and second arms.

23. The x-ray apparatus of claim 17, for use in three-dimensional imaging of a human breast with different projection angles.

24. The x-ray apparatus of claim 17, wherein said compression arrangement comprises a first and a second actuator arm connected to said paddle at end portions of said paddle and said arms being arranged to move independently.

25. The x-ray apparatus of claim 17, wherein said compression arrangement comprises a first and a second actuator arm connected to said paddle, said arms being arranged to rotate around each rotating axis, and said paddle being slidebly connected to said first and second arms.

26. The x-ray apparatus of claim 17, further comprising a means for automatically setting which edge to follow said field, and said means automatically depends on another mode of operation in said x-ray apparatus.

27. The x-ray apparatus of claim 17, being an apparatus for MLO or other tilted angle.

28. The x-ray apparatus of claim 27, wherein a second edge is within the x-ray field but not within the object image field and excluded from the image.

29. The x-ray apparatus of claim 17, wherein the compression paddle is inside the x-ray field, with at least one of its edges immediately outside the x-ray field when compressing the object during x-ray imaging.

30. An x-ray apparatus for three-dimensional imaging of a human breast comprising a compression arrangement, said compression arrangement comprising a compression paddle, a guide and an actuator arrangement for displacement of said compression paddle along said guide, wherein the direction of said guide is adjustable, whereby an edge of said compression paddle essentially follows an angled boundary of a three-dimensional image field.

31. The x-ray apparatus according to claim 30, further comprising a means for automatically setting said direction of said guide depending on an angle of said apparatus or type of examination.

32. A compression arrangement for use in an x-ray imaging apparatus, said arrangement comprising a compression paddle and an actuator for displacing said compression paddle along a trajectory, and an arrangement for tilting said paddle in said trajectory, said paddle having an extension direction substantially transverse to an object insertion direction, wherein said means is operatively arranged to incline said trajectory of said paddle along said extension direction, whereby said trajectory is arrangable to follow a first or a second inclined boundary of said image field.

* * * * *